United States Patent
Narang et al.

(10) Patent No.: US 6,455,064 B1
(45) Date of Patent: Sep. 24, 2002

(54) METHOD OF APPLYING AN ADHESIVE COMPOSITION OVER A BIOACTIVE POLYMERIZATION INITIATOR OR ACCELERATOR

(75) Inventors: Upvan Narang; Daniel L. Hedgpeth; Gabriel N. Szabo, all of Raleigh; Ibraheem T. Badejo, Morrisville; Joe B. Barefoot, Raleigh, all of NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/430,176

(22) Filed: Oct. 29, 1999

Related U.S. Application Data

(63) Continuation-in-part of application No. 09/069,875, filed on Apr. 30, 1998.

(51) Int. Cl.[7] .................................................. A61K 9/70
(52) U.S. Cl. ........................ 424/447; 424/443; 424/445; 424/78.06
(58) Field of Search ........................... 424/78.06, 443, 424/445, 447

(56) References Cited

U.S. PATENT DOCUMENTS

| | | |
|---|---|---|
| 2,721,858 A | 10/1955 | Joyner et al. |
| 3,254,111 A | 5/1966 | Hawkins et al. |
| 3,483,870 A | 12/1969 | Coover et al. |
| 3,554,990 A | 1/1971 | Quinn et al. |
| 3,940,362 A | 2/1976 | Overhults |
| 3,964,643 A | 6/1976 | Morane et al. |
| 3,995,641 A | 12/1976 | Kronenthal et al. |
| 4,042,442 A | 8/1977 | Dombroski et al. |
| 4,125,494 A | 11/1978 | Schoenberg et al. |
| 4,127,382 A | 11/1978 | Perry |
| 4,315,998 A | 2/1982 | Neckers et al. |
| 4,359,454 A | 11/1982 | Hoffman |
| 4,364,876 A | 12/1982 | Kimura et al. |
| 4,532,183 A | 7/1985 | Shackle et al. |
| 4,669,491 A | 6/1987 | Weisberg et al. |
| 4,720,513 A | 1/1988 | Kameyama et al. |
| 4,764,377 A | 8/1988 | Goodson |
| 4,797,282 A | 1/1989 | Wahlig et al. |
| 4,856,504 A | 8/1989 | Yamamoto et al. |
| 4,892,736 A | 1/1990 | Goodson |
| 4,915,694 A | 4/1990 | Yamamoto et al. |
| 4,940,579 A | 7/1990 | Randen |
| 4,980,086 A | 12/1990 | Hiraiwa et al. |
| 5,061,286 A | 10/1991 | Lyle |
| 5,254,132 A | 10/1993 | Barley et al. |
| 5,259,835 A | 11/1993 | Clark et al. |
| 5,262,200 A | 11/1993 | Puder et al. |
| 5,324,520 A | 6/1994 | Dunn et al. |
| 5,328,687 A | 7/1994 | Leung et al. |
| 5,480,935 A | 1/1996 | Greff et al. |
| 5,514,371 A | 5/1996 | Leung et al. |
| 5,514,372 A | 5/1996 | Leung et al. |
| 5,575,997 A | 11/1996 | Leung et al. |
| 5,580,565 A | 12/1996 | Tighe et al. |
| 5,582,834 A | 12/1996 | Leung et al. |
| 5,624,669 A | 4/1997 | Leung et al. |
| 5,656,286 A | 8/1997 | Miranda et al. |
| 5,684,042 A | 11/1997 | Greff et al. |
| 5,753,699 A | 5/1998 | Greff et al. |
| 5,762,919 A | 6/1998 | Greff et al. |
| 5,762,955 A | 6/1998 | Smith |
| 5,783,177 A | 7/1998 | Greff et al. |
| 5,811,471 A | 9/1998 | Shanbrom |
| 5,866,106 A | 2/1999 | Papay |
| 5,900,245 A | 5/1999 | Sawhney et al. |
| 5,928,611 A | 7/1999 | Leung |
| 5,981,621 A | * 11/1999 | Clark et al. |
| 6,001,213 A | 12/1999 | Liu |
| 6,090,397 A | 7/2000 | Lee et al. |
| 6,155,265 A | 12/2000 | Hammerslag |

FOREIGN PATENT DOCUMENTS

| | | |
|---|---|---|
| DE | 3228237 | 2/1983 |
| EP | 0 170 526 | 2/1986 |
| EP | 247726 | 12/1987 |
| EP | 341391 | 11/1989 |
| EP | 575976 | 12/1993 |
| EP | 0 865 787 | 9/1998 |
| JP | 61-228054 | 10/1986 |
| JP | 63-301806 | 12/1988 |
| JP | 04-313341 | 11/1992 |
| JP | 06-269658 | 9/1994 |
| JP | 09-52814 | 2/1997 |
| RO | 81169 | 1/1983 |
| WO | 92/12218 | 6/1993 |
| WO | 95/09607 | 4/1995 |
| WO | 96/40797 | 12/1996 |
| WO | 9/13921 | 3/1999 |
| WO | 99/20258 | 4/1999 |
| WO | 99/21725 | 5/1999 |
| WO | 99/23010 | 5/1999 |
| WO | 99/23011 | 5/1999 |
| WO | 99/23150 | 5/1999 |
| WO | 99/55374 | 11/1999 |
| WO | 00/38777 | 7/2000 |

OTHER PUBLICATIONS

Lars Wetter et al., "Effects of Zinc Oxide in an Occlusive, Adhesive Dressing on Granulation Tissue Formation," *Acta Pharmacol Toxicol Suppl,* vol. 59(7), pp. 184–187 (1986).

Lars Wetter et al., "Effects of Zinc Oxide in an Occlusive Adhesive Dressing on Granulation Tissue Formation," *Scand. J. Plast. Reconsr. Surgery,* vol. 20, pp. 165–172 (1986).

(List continued on next page.)

*Primary Examiner*—Jose' G. Dees
*Assistant Examiner*—Michael A. Williamson
(74) *Attorney, Agent, or Firm*—Oliff & Berridge, PLC

(57) ABSTRACT

A composition comprising a polymerizable adhesive monomer is applied over a biologically active initiator or accelerator for polymerization of the monomer. The biologically active initiator or accelerator is a medicament that provides a desired medical or therapeutic activity as well as enhancing polymerization of the adhesive.

47 Claims, No Drawings

OTHER PUBLICATIONS

M. Fan et al., "Effect of Chlorhexidine Varnish System on Streptococcus Mutant in Fissure Plaques," *Zhonghua Kougiang Yixue Zazhi,* vol. 32, No. 5, pp. 269–271 (1997).

S. Sonis et al., "Cyanoacrylate as an Adhesive for Other Medicaments: A Study with Triamcinalone on the Healing of Experimental Oral Ulcers", *Pharmacology and Therapeutics in Dentistry,* vol. 2, pp. 147–156, (1975).

M. Tonetti et al., "Zero–Order Delivery with Periodontal Placement of Tetracycline–Loaded Ethylene Vinyl Acetate Fibers", *J. Periodont Res.,* vol. 25, pp. 243–249, (1990).

J. Goodson, "Treatment of Periodontal Diseases by Local Drug Delivery", *Recent Advances in Periodontology,* vol. 11, pp. 61–68, (1991).

* cited by examiner

METHOD OF APPLYING AN ADHESIVE COMPOSITION OVER A BIOACTIVE POLYMERIZATION INITIATOR OR ACCELERATOR

This application is a continuation-in-part of U.S. patent application Ser. No. 09/069,875, filed Apr. 30, 1998, the entire disclosure of which is incorporated herein by reference.

BACKGROUND OF THE INVENTION

1. Field of Invention

The invention relates to the use of monomer and polymer compositions as biomedical adhesives and sealants, and particularly to their use in conjunction with bioactive materials.

2. Description of Related Art

Products in primary use for wound closure are surgical sutures and staples. Sutures are recognized to provide adequate wound support. However, sutures cause additional trauma to the wound site (by reason of the need for the needle and suture to pass through tissue and the need to anesthetize the wound area via needle puncture) and are time-consuming to place, and, at skin level, can cause unattractive wound closure marks. Surgical staples have been developed to speed wound apposition and provide improved cosmetic results. However, surgical staples also impose additional wound trauma and require the use of ancillary and often expensive devices for positioning and applying the staples. Both sutures and staples are especially problematic in pediatric cases where the patient may have a strong fear response and refuse to cooperate with their placement, and in geriatric cases where the skin tissue is weaker and prone to tearing.

As an alternate to surgical sutures and staples, adhesives have been used in wound closure. Similarly, adhesives have been proposed for use in wound covering and protection in such topical applications as minor cuts, scrapes, irritations, compromised skin, surface lacerations, abrasions, burns, stomatitis, and other open surface wounds. One group of such adhesives is the 1,1-disubstituted ethylene monomers, such as the monomeric forms of α-cyanoacrylates.

For wound closure and covering using adhesives, mixtures of cyanoacrylate adhesives and medicaments have been developed. For example, U.S. Pat. No. 5,684,042 to Greff et al. discloses a cyanoacrylate composition comprising an antimicrobially-effective amount of an iodine-containing antimicrobial agent. The iodine-containing antimicrobial agent is dispersible in the cyanoacrylate composition and does not cause premature polymerization of the cyanoacrylate adhesive (i.e., does not initiate polymerization).

U.S. Pat. No. 3,483,870 to Coover, et al. discloses the use of methyl α-cyanoacrylate as a bone cement. The α-cyanoacrylate may be blended with antibiotics so long as the antibiotics do not cause early polymerization (i.e., do not act as polymerization initiators) or cause adverse effects on the healing process.

Another method for treating or preventing infections associated with wounding using adhesives involves layering a cyanoacrylate over a medicament on a wound site. For example, U.S. Pat. No. 5,580,565 to Tighe, et al. discloses the use of a topical α-cyanoacrylate tissue adhesive to form a protective barrier over intact or broken skin to allow healing of the skin to occur. Polymerization of the α-cyanoacrylate adhesive is initiated by contact with skin moisture and tissue protein. Tighe et al. also disclose the use of α-cyanoacrylate adhesives as a protective layer over medicaments. The only medicament exemplified by Tighe et al. is cortisone, which does not initiate polymerization of cyanoacrylate monomer compositions.

Others have also disclosed the use of cyanoacrylate adhesives as coverings for medicaments. For example, Beasley et al. disclose application of antibiotics, such as vancomycin powder or tetracycline, to a wound, followed by covering of the wound with isobutyl cyanoacrylate. This type of treatment is disclosed as showing promise for treatment of bacterially infected tissues. (Beasley, J. D. et al., *Effect of Antibiotics and Chemical Adhesives on Infected Wounds*, Mil. Med. 136(6):566–569, 1971). However, neither of these antibiotics act to initiate polymerization of the cyanoacrylate.

The use of cyanoacrylate adhesives to cover bioactive agents is also disclosed in: Miles et al., Oral Surgery, Oral Medicine, Oral Pathology, Vol. 75, No. 3,397–402 (using triamcinolone acetonide (Kenalog) or chlorhexidine digluconate (Peridex) as the bioactive agent); and Kaufman, R. S., The Laryngoscope, 1974, 793–804 (using dexamethasone sodium phosphate (Decadron) as the bioactive agent).

U.S. Pat. No. 4,669,491 to Weisberg et al. discloses the use of biocides covered by protective acrylic artificial nails. The biocides may be acidic or phenolic, but are preferably selected so as not to affect the cure rate or the bond strength of the glue layer. They include thymol, chlorothymol, benzoic acid, p-hydroxybenzoate alkyl esters, 4- and 6-phenyl-2-chlorophenyl, carvocrol, hexachlorophene, nitroforans, allicin, 2-phenylphenol, boric acid, mercurials, and such antibiotics as Bacitracin and Griseofulvin, quaternary ammonium halides such as n-alkyldirnethylbenzylammonium chloride, cetyl pyridinium bromide, 5-methyl-2-isopropyl-cyclohexanol, 2-bornanone, cineole, safrole, bornyl chloride, 2-phenoxyethanol, benzylalcohol and ethanol. The biocides are applied to human fingernails, then covered by solutions comprising cyanoacrylate adhesive. The biocides are applied to the natural fingernails in a solution, and the solution is allowed to dry, leaving the active biocides on the nails. The biocide-treated fingernails are roughened with an abrasive, then coated with a monomeric cyanoacrylate solution to form the artificial fingernails. The cyanoacrylate monomers are polymerized by the addition of a polymethacrylate ester composition containing a benzoyl peroxide catalyst. There is no suggestion of selecting the monomers and biocides such that the biocides affect polymerization.

U.S. Pat. Nos. 4,764,377 and 4,892,736 to Goodson disclose the use of a therapeutic agent and a cyanoacrylate adhesive for treatment of periodontal diseases. The therapeutic agent is placed within the periodontal pocket, then covered by a mechanical maintenance system (which may be in the form of a layer of an adhesive film, such as n-butylcyanoacrylate), which holds the therapeutic agent in the periodontal pocket, allowing the therapeutic agent to be administered to the periodontal site. Goodson and co-workers also disclose this type of system in, for example, "J. Periodont. Res", 1990, Vol. 25, 243–249, and "Recent Advances in Periodontology", Vol. 11,61–68. The therapeutic agents include antibacterial agents such as iodine, sulfonamides, mercurials, bisbiguanides, or phenolics; antibiotics such as tetracycline, neomycin, kanamycin, metranidazole, or canamycin; anti-inflammatory agents such as indomethacin, eugenol, or hydrocortisone; immunosuppressive or stimulatory agents such as methotrexate or levamasole; dentinal desensitizing agents such as strontium chloride or sodium fluoride; odor masking agents such as peppermint oil or chlorophyll; immune reagents such as immunoglobulin or antigens; local anesthetic agents such as lidocaine or benzocaine; nutritional agents such as amino acids, essential fats, and vitamin C; antioxidants such as alphatocopherol and butylated hydroxy toluene; lipopolysaccharide complexing agents such as polymyxin; or peroxides such as urea peroxide. There is no suggestion of selecting the monomers and biocides such that the biocides affect polymerization.

U.S. Pat. Nos. 5,514,371 and 5,624,669 to Leung, et al. disclose the addition of a therapeutic agent in a cyanoacrylate composition. The cyanoacrylate adhesive forms a matrix for the therapeutic agent, with the therapeutic agent being released in vivo over time from the matrix during biodegradation of the polymer. The therapeutic agent is not used as a polymerization initiator or a polymerization rate modifier.

U.S. Pat. No. 4,940,579 to Randen discloses a composition comprising a medicament and a cyanoacrylate adhesive. The composition is used to deliver medicaments to non-mucosal areas of mammal bodies. However, Randen does not disclose the use of medicaments as polymerization initiators and/or rate accelerators.

U.S. Pat. No. 5,254,132 to Barley et al. discloses the use of cyanoacrylate adhesives in conjunction with antibiotics. The antibiotics are added to the cyanoacrylate compositions and stored in a sterile applicator for use in a single-dose application. The composition is maintained in a sealed container to avoid polymerization prior to application; therefore, the antibiotic does not initiate or accelerate polymerization of the adhesive composition.

Typically, when used in medical applications, cyanoacrylate adhesives are applied in monomeric form to the surfaces to be joined, sealed, or otherwise treated. Typically, in situ anionic polymerization of the monomer occurs, giving rise to the desired adhesive bond or covering. Initiation of polymerization in situ typically utilizes moisture and/or proteins naturally present in the tissue being treated. Thus, in applications where tissue fluids are present, it is not necessary to add polymerization initiators or rate accelerators to cyanoacrylate composition. However, sometimes it is desirable to apply the cyanoacrylate adhesives to dry tissues (i.e., tissues that are essentially free of tissue fluids or the like). In addition, to prolong the shelf life of these extremely reactive cyanoacrylate monomers, they are formulated with stabilizers to avoid their premature polymerization. In these situations, polymerization of the cyanoacrylate adhesive proceeds slowly, causing inconvenience to the user. To overcome this inconvenience, polymerization initiators and/or rate accelerators have been added to the cyanoacrylate adhesive composition.

When an initiator or accelerator is added to the composition, it is not added until immediately prior to application of the adhesive. For example, U.S. Pat. No. 4,042,442 to Dombroski et al. discloses the addition of a polymerization initiator (either caffeine or theobromine) to a cyanoacrylate adhesive composition. The caffeine or theobromine is added to the adhesive composition in one of two ways. In the first way, the caffeine or theobromine can be mixed with the cyanoacrylate adhesive composition by stirring just prior to application of the adhesive to the substrates to be joined. In the second way, the caffeine or theobromine is dissolved in a volatile solvent, applied to the surfaces to be joined, the volatile solvent is allowed to evaporate, and then the cyanoacrylate adhesive composition is applied to the surfaces of the substrates to be joined.

Commonly assigned U.S. Pat. No. 5,928,611 (corresponding to earlier-published PCT Application No. WO 96/40797), the disclosure of which is hereby incorporated in its entirety, discloses the incorporation of a polymerization initiator or polymerization rate modifier in an applicator tip. Incorporation of the initiator or the rate modifier into the applicator tip allows a level of control over the polymerization rate that cannot be achieved through reliance on polymerization initiators naturally present at the wound site. Incorporation of the initiator and/or rate modifier into the applicator tip provides convenience to the user, since a single applicator is required, and no additional mixing is needed. However, this application does not disclose the use of a medicament as an initiator or accelerator of polymerization for monomeric cyanoacrylate compositions.

U.S. Pat. No. 5,866,106 to Papay discloses the addition of vitamins and minerals in a cyanoacrylate composition. The cyanoacrylate adhesive composition is disclosed as useful for an adhesive for bonding nail tips, and for forming a nail polish product.

Commonly assigned U.S. patent application Ser. No. 09/343,914, filed Jun. 30, 1999, discloses monomeric adhesive composition comprising a polymerizable 1,1-disubstituted ethylene monomer and a flavoring additive, and methods of making and using such a composition. In these compositions, the flavoring additive is mixed directly with the monomeric adhesive.

Although the use of medicaments in conjunction with cyanoacrylate adhesive compositions is known, and the use of polymerization initiators with cyanoacrylate adhesive compositions is known, there exists a need to provide a method for delivering pharmaceutically-effective levels of medicaments to wound sites along with cyanoacrylate adhesives that is convenient, reliable, and effective. To address this need, the present invention provides methods and compositions that use pharmaceutically-effective amounts of medicaments as polymerization initiators or accelerators for monomeric adhesive compositions.

SUMMARY OF THE INVENTION

According to the present invention, a medicament acts as both an initiator and/or an accelerator of polymerization of a monomeric adhesive composition and as a pharmaceutically active material. As used herein, a polymerization initiator is any material that causes a cyanoacrylate composition applied to a substantially dry tissue (i.e., in the substantial absence of plasma or like tissue fluids) to polymerize in less than 300 seconds at ambient temperature, for example approximately 21–25° C. Preferably, the initiator causes the cyanoacrylate composition to polymerize in less than 150 seconds, or more preferably less than 135 seconds at ambient temperature, for example, at approximately 21–25° C. As used herein, a polymerization accelerator is any material that accelerates the rate of polymerization of a cyanoacrylate composition such that polymerization that would normally take more than 300 seconds at ambient temperature, for example at approximately 21–25° C. occurs in less than 300 seconds, preferably in less than 150 seconds, and more preferably in less than 135 seconds. The initiator or rate accelerator can be, for example, a catalyst, but can also be a material that is consumed or chemically modified during the polymerization reaction. The medicament can be any material that has both a pharmaceutical effect as applied and a polymerization initiating or rate accelerating activity, including, but not limited to, antibiotics, antimicrobials, antiseptics, bacteriocins, bacteriostats, disinfectants, steroids, anesthetics, antifingal agents, anti-inflammatory agents, antibacterial agents, antiviral agents, antitumor agents, and tissue growth promoting substances.

The invention provides, among other things, a method of closing, sealing, covering, and/or protecting deep and/or surface wounds, such as those resulting from surgery or from minor cuts, scrapes, irritations, compromised skin, lacerations, burns, sores, abrasions, and the like. The method includes laying down a medicament onto a wound or sore and applying over the medicament a polymerizable monomer-containing composition whose polymerization is initiated or accelerated by the medicament.

In embodiments, the invention also provides a method of delivering a medicament locally or systemically to a human or animal by applying the medicament to a tissue site and applying over the medicament a polymerizable monomer-containing composition whose polymerization is initiated or accelerated by the medicament. As used herein, tissue includes any tissue of a human or animal, such as skin, mucous membranes, oral/nasal tissues, gastrointestinal tissues, organ tissues, tumors, non-keratinous tissue, etc.

The present invention also provides a kit comprising a saleable package containing (i) a container of a polymerizable monomer composition as described herein, and (ii) a container of a medicament, preferably one that acts as a polymerization initiator or polymerization rate modifier for said monomer composition. The containers can preferably be in the form of, or part of, an applicator or applicator system and are preferably sterilizable. For example, the package and its contents can preferably be sterilized simultaneously.

The present invention provides several advantages over wound treating methods now in use, including the ability to:
a) control the molecular weight distribution of the polymerized or cross-linked material (through the use of the polymerization initiator and/or polymerization rate accelerator);
b) control the setting time of the polymerized or cross-linked cyanoacrylate adhesive;
c) control the flow properties of polymerizable cyanoacrylate compositions;
d) provide a medicament to a patient while simultaneously providing wound closure, protection, and/or coverage;
e) provide a medicament to a patient through topical administration; and/or
f) any combination of the above.

DETAILED DESCRIPTION OF PREFERRED EMBODIMENTS

According to the invention, a medicament is applied to a tissue prior to application of the monomer-containing composition. The medicament acts to initiate and/or accelerate polymerization of the monomer composition. Thus, the medicament provides not only a biological activity, but a chemical one as well.

Examples of such medicaments include, but are not limited to antibiotics, antimicrobials, antiseptics, bacteriocins, bacteriostats, disinfectants, steroids, anesthetics, antifungal agents, anti-inflammatory agents, antibacterial agents, antiviral agents, antitumor agents, growth promoters, and mixtures thereof.

Exemplary medicaments include, but are not limited to, quaternary ammonium halides such as benzalkonium chloride and benzethonium chloride; chlorhexidine sulfate; gentamicin sulfate; hydrogen peroxide; quinolone thioureas; silver salts, including, but not limited to, silver acetate, silver benzoate, silver carbonate, silver chloride, silver citrate, silver iodide, silver nitrate, and silver sulfate; copper compounds, including but not limited to copper chloride, copper sulfate, and copper peptides as discussed, for example, in "Copper: An Essential Element for Life," ProCyte Corporation, available at http://www.humatech.com/technology.html Oct. 28, 1999, the entire disclosure of which is incorporated herein by reference; sodium hypochlorite; salts of sulfadiazine, including, but not limited to silver, sodium, and zinc complexes and salts; antioxidants such as vitamins such as vitamin E, other agents mentioned above; and mixtures thereof.

Preferable medicaments are those that are anions or help in radical generation or that are ion pairs or are themselves radicals.

In embodiments, the medicament is preferably a quaternary ammonium halide such as alkylbenzyldimethylammonium chloride (benzalkonium chloride; BAC) with an alkyl containing 6–18 carbon atoms, its pure components, or mixtures thereof, or benzethonium chloride; or a salt of sulfadiazine, such as a silver, sodium, or zinc salt.

Another example of a medicament that possesses polymerization initiation and antiviral, antimicrobial, and/or antifingal properties is Gentian Violet, also known as crystal violet or methylrosaniline chloride. Examples of materials that possess polymerization initiation and wound healing properties also include various zinc complexes and zinc salts, antioxidants such as vitamin E and other vitamins and the like, and copper compounds such as copper chloride, copper sulfate and copper peptides.

Crystal violet has many benefits, particularly when used in conjunction with the adhesive monomer compositions of the present invention. One benefit of crystal violet is that in addition to providing the antiviral, antimicrobial and/or antifimgal effects, it also provides a visible color at the site of application, which can help ensure that a sufficient or desired amount of adhesive has been applied. However, whereas crystal violet is known to leave "tattoo" scars on tissue when it is applied, such tattoo scarring does not result when used in combination with the adhesive monomer compositions of the present invention. Rather, the crystal violet provides its coloring and other effects, without leaving a long-term or permanent mark.

Suitable zinc complexes and salts include, but are not limited to, zinc salts of cyanoacrylic acid, zinc salts of cyanoacetic acid, zinc salts of dicyanoglutaric acid, zinc salts of rosin, zinc oxide, zinc salts of polycyanoacrylic acid, zinc salts of polyacrylic acid, zinc bacitracin, zinc salicylate, zinc stearate, zinc citrate, zinc lactate, mixtures thereof, and the like. Preferably, the zinc compounds are of $Zn^{2+}$. Such zinc compounds are particularly effective in promoting healing of leg ulcers, thermal bums, and the like.

The medicaments can be tested for initiation ability by pipetting an appropriate volume of a solution of the medicament prepared in a volatile solvent in a differential scanning calorimetric aluminum pan. The volatile solvent is allowed to dry under ambient conditions. Alternatively, the appropriate quantity of the medicament is dispensed directly onto the differential scanning calorimetric pan. In either of the abovementioned cases, 25 µl of the chosen monomer solution is pipetted into the pan. The time taken for the monomer composition to polymerize to the point of a gel is the polymerization time.

In embodiments, the composition can comprise other polymerization initiators and/or rate accelerators in addition to the medicament. Particular additional initiators for particular systems may be readily selected by one of skill in the art without undue experimentation. Suitable additional polymerization initiators for the cyanoacrylate compositions include, but are not limited to, other medicaments; detergent compositions; surfactants: e.g., nonionic surfactants such as polysorbate 20 (e.g., Tween 20™; ICI Americas), polysorbate 80 (e.g., Tween 80™; ICI Americas), and poloxamers; cationic surfactants such as tetrabutylammonium bromide and benzethonium chloride or its pure components; anionic surfactants such as, stannous octoate (tin (II) 2-ethylhexanoate), and sodium tetradecyl sulfate; and amphoteric or zwitterionic surfactants such as dodecyldimethyl(3-sulfopropyl) ammonium hydroxide, inner salt; amines, imines and amides, such as imidazole, tryptamine, urea, arginine and povidine; phosphines, phosphites and phosphonium salts, such as triphenylphosphine and triethyl phosphite; alcohols such as ethylene glycol; methyl gallate; ascorbic acid; tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™336 (General Mills, Minneapolis, Min.); organometallics; manganese acetylacetonate; and radical initiators and radicals, such as di-t-butyl peroxide and azobisisobutyronitrile.

The polymerizable and/or cross-linkable material may also contain an initiator which is inactive until activated by a catalyst or accelerator (included within the scope of the term "initiator" as used herein). These initiators can be activated by appropriate stimulation such as heat and/or light (e.g., ultraviolet or visible light).

Compositions employed in the invention are preferably sterilizable.

The amount of medicament applied should be an amount sufficient to cause initiation or acceleration of the rate of polymerization upon contact and mixing of the medicament with the monomeric composition. The medicament should also be applied in a pharmaceutically-effective amount and should be selected in conjunction with the specific polymerizable monomeric compound such that the medicament will function as a polymerization initiator and/or rate accelerator for the chosen monomer. Such a selection process can easily be performed by one of skill in the art.

The medicament can have a pharmaceutical effect only at the site of application (i.e., limited to the tissue on/in which it is applied), or it can have a systemic effect (by systemic, it is not only meant that the medicament has an effect throughout the patient's body, but also at a specific site other than the site of application). In embodiments where the medicament is applied in an amount sufficient to show a systemic pharmaceutical activity, it can be absorbed, transported, or otherwise distributed to the site or sites within the patient where the pharmaceutical activity is desired, e.g., through the cardiovascular or lymph systems.

Depending on the particular requirements of the user, the medicament and adhesive compositions of this invention can be applied by any appropriate device, which can be the same or different for the medicament and adhesive composition. Examples include, but are not limited to, a glass stirring rod, sterile brush, medicine dropper, or an applicator containing a crushable ampoule and an applicator tip, as disclosed in U.S. Pat. No. 5,928,611, the entire disclosure of which is incorporated herein by reference. In many situations a pump or pressurized aerosol dispensing package is preferred in which the adhesive composition is in solution with a compatible anhydrous propellant. A preferred device is an absorbent swab or wipe.

The medicament may be in the form of a solid, such as a powder or a solid film, or in the form of a liquid, such as a watery, viscous, or paste-like material. The medicament may also be compounded with a variety of additives, such as surfactants or emulsifiers, and vehicles.

The methods of this invention can be used to join together two surfaces, as a replacement for or in addition to sutures, by applying the present compositions to opposing wound surfaces that are then held together while polymerization proceeds. The methods of this invention can also be used to coat, protect, or otherwise cover surface, superficial, or otherwise topical wounds or pathologies including, but not limited to, minor cuts, scrapes, irritations, compromised skin, superficial lacerations, abrasions, burns, sores, and stomatitis. The methods of the invention can also be used on tissues that do not show any signs of tissue damage. For example, the methods can be used to deliver medicaments to a patient through healthy tissue. They can also be used, for example, to locally deliver medicaments to tissues such as tumors or organs.

In one embodiment, the present invention provides a replacement for sutures and includes a method of delivering a medicament to a tissue by forming a biocompatible film across abutted tissue surfaces, comprising: (a) holding together at least two tissue surfaces to form abutted surfaces, (b) applying a medicament which is a polymerization initiator or polymerization rate accelerator to the abutted tissue surfaces, (c) applying on to the medicament and across the abutted tissue surfaces a polymerizable adhesive monomer composition, and (d) allowing the composition to polymerize and form a biocompatible film on the abutted tissue surfaces. A subsequent coating may be applied immediately after application of a previous coating or after a previous coating has been completely polymerized. Preferably, the monomer composition applied to the abutted tissue surface is allowed to at least partially polymerize prior to subsequent coatings or applications of additional monomer composition. A coating of an adhesive composition having a monomer different from the monomer of the first or previous coating may be applied as the second or subsequent coating.

Addition of a plasticizing agent and acidic stabilizing agent can cause such a polymer coating to have sufficient bond strength and flexibility even with significant film or coating thicknesses. Suitable film thickness range from 0.1 mm to 2.0 mm or 3.0 mm or higher, preferably from 0.2 mm to 1.5 mm, and more preferably from 0.4 mm to 0.8 mm.

In embodiments, the biocompatible film formed as a replacement for sutures may have an in vivo film strength of at least 70 mm Hg of vacuum pressure required to induce wound failure, generally from 70 mm Hg to 400 mm Hg of vacuum pressure required to induce wound failure, preferably from 90 mm Hg to 400 mm Hg of vacuum pressure required to induce wound failure, and more preferably from 100 mm Hg to 400 mm Hg of pressure required to induce wound failure.

When repairing injured tissues (for example, to control bleeding), the invention comprises first sponging the site to be repaired to remove superficial or body tissue fluids. Desired bonding of tissues or hemostasis can also proceed well in the presence of blood and other body fluids as well as on dry tissue. The bonds formed are of adequate flexibility and strength to withstand normal movement of tissue. In addition, bond strength is maintained as natural wound healing proceeds.

In another embodiment, the present invention is directed to a method of treating a superficial or topical pathology, including, but not limited to a skin wound such as a minor cut, scrape, irritation, compromised skin, superficial laceration, burn, or abrasion, or a sore on a mucous membrane. The method comprises (a) applying a medicament that is a polymerization initiator or rate accelerator to the affected tissue, (b) applying a polymerizable monomer-containing composition over the medicament; (c) allowing the composition to polymerize; and (d) optionally, applying the composition at least once more to the same site.

Suitable film thickness for such topical applications is preferably between 1 and 10,000 μm, for example between 1 and 1000 μm. In embodiments, the biocompatible film so formed may have a film strength of at least 5 mm Hg, such as 5–400 mm Hg, preferably from 50–400 mm Hg.

In embodiments, the present invention provides a method of delivering a medicament to a tissue by (a) applying a medicament that is a polymerization initiator and/or polymerization rate accelerator to a site (e.g., directly to tissue); (b) applying a polymerizable monomer-containing composition over the medicament; and (c) optionally, applying the composition at least once more to the same site. Suitable film thickness and strength are preferably those disclosed above for other uses.

In embodiments, the medicament is released to the tissue to which it is in contact at a constant, or near constant, rate over a period of time while in contact with the affected tissue.

The present invention also provides a kit for delivering a medicament to a patient. The kit comprises a container with a polymerizable monomer composition, such as a cyanoacrylate adhesive. The kit also comprises another container with a medicament. The medicament is selected so that it functions in conjunction with the co-packaged polymerizable monomer composition to initiate polymerization of the monomer or modify (e.g., accelerate) the rate of polymerization for the monomer to form a polymeric adhesive. The proper combination of medicament and polymerizable monomer can be determined easily by one of skill in the art. The medicament is supplied in the kit in an amount that will be pharmaceutically effective when applied topically (i.e., directly to tissue). A separate container of flavorant may also optionally be included in the kit.

The monomer composition, in embodiments, is preferably a monomeric (including prepolymeric) adhesive composition. In embodiments, the monomer is a 1,1-disubstituted ethylene monomer, e.g., an α-cyanoacrylate. Preferred monomer compositions of the present invention and polymers formed therefrom are useful as tissue adhesives, sealants for preventing bleeding or for covering open wounds, and in other biomedical applications. They find uses in, for example, apposing surgically incised or traumatically lacerated tissues; retarding blood flow from wounds; drug delivery; dressing burns; dressing skin or other superficial or surface wounds (such as abrasions, chaffed or raw skin, and/or stomatitis); and aiding repair and regrowth of living tissue.

Monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. No. 5,328,687 to Leung, et al., which is hereby incorporated in its entirety by reference herein.

Useful 1,1-disubstituted ethylene monomers include, but are not limited to, monomers of the formula:

$$HRC=CXY \qquad (I)$$

wherein X and Y are each strong electron withdrawing groups, and R is H, $-CH=CH_2$ or, provided that X and Y are both cyano groups, a $C_1-C_4$ alkyl group.

Examples of monomers within the scope of formula (I) include alpha-cyanoacrylates, vinylidene cyanides, $C_1-C_4$ alkyl homologues of vinylidene cyanides, dialkyl methylene malonates, acylacrylonitriles, vinyl sulfinates and vinyl sulfonates of the formula $CH_2=CX'Y'$ wherein X' is $-SO_2R'$ or $-SO_3R'$ and Y' is $-CN, -COOR', -COCH_3, -SO_2R'$ or $-SO_3R'$, and R' is H or hydrocarbyl.

Preferred monomers of formula (I) for use in this invention are alpha-cyanoacrylates. These monomers are known in the art and have the formula:

$$(II)$$

wherein $R^2$ is hydrogen and $R^3$ is a hydrocarbyl or substituted hydrocarbyl group; a group having the formula $-R^4-O-R^5-O-R^6$ or the formula $-R^5-O-R^6$, wherein $R^4$ is a 1,2-alkylene group having 2–4 carbon atoms, $R_5$ is an alkylene group having 2–4 carbon atoms, and $R^6$ is an alkyl group having 1–6 carbon atoms; or a group having the formula:

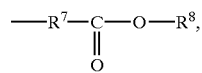

wherein $R^7$ is:

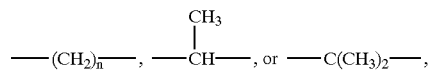

wherein n is 1–10, preferably 1–5 carbon atoms and $R^8$ is an organic moiety.

Examples of suitable hydrocarbyl and substituted hydrocarbyl groups include straight chain or branched chain alkyl groups having 1–16 carbon atoms; straight chain or branched chain $C_1-C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety $R^8$ may be substituted or unsubstituted and may be straight chain, branched or cyclic, saturated, unsaturated or aromatic. Examples of such organic moieties include $C_1-C_8$ alkyl moieties, $C_2-C_8$ alkenyl moieties, $C_2-C_8$ alkynyl moieties, $C_3-C_{12}$ cycloaliphatic moieties, aryl moieties such as phenyl and substituted phenyl and aralkyl moieties such as benzyl, methylbenzyl and phenylethyl. Other organic moieties include substituted hydrocarbon moieties, such as halo (e.g., chloro-, fluoro- and bromo-substituted hydrocarbons) and oxy- (e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof Particularly preferred are alkyl moieties of 4 to 6 carbon atoms.

In the cyanoacrylate monomer of formula (II), $R^3$ is preferably an alkyl group having 1–10 carbon atoms or a group having the formula —$AOR^9$, wherein A is a divalent straight or branched chain alkylene or oxyalkylene moiety having 2–8 carbon atoms, and $R^9$ is a straight or branched alkyl moiety having 1–8 carbon atoms.

Examples of groups represented by the formula -$AOR^9$ include 1-methoxy-2-propyl, 2-butoxy ethyl, isopropoxy ethyl, 2-methoxy ethyl, and 2-ethoxy ethyl.

Preferred α-cyanoacrylate monomers used in this invention include 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate.

The α-cyanoacrylates of formula (II) can be prepared according to methods known in the art. U.S. Pat. Nos. 2,721,858 and 3,254,111, each of which is hereby incorporated in their entirety by reference herein, disclose methods for preparing α-cyanoacrylates. For example, the α-cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The α-cyanoacrylate monomers prepared with low moisture content and essentially free of impurities are preferred for biomedical use.

The α-cyanoacrylates of formula (II) wherein $R^3$ is a group having the formula —$R^4$—O—$R^5$—O—$R^6$ or the formula —$R^5$—O—$R^6$ can be prepared according to the method disclosed in U.S. Pat. No. 4,364,876 to Kimura et al., which is hereby incorporated in its entirety by reference. In the Kimura et al. method, the α-cyanoacrylates are prepared by producing a cyanoacetate by esterifying cyanoacetic acid with an alcohol or by transesterifying an alkyl cyanoacetate and an alcohol; condensing the cyanoacetate and formaldehyde or para-formaldehyde in the presence of a catalyst at a molar ratio of 0.5–1.5:1, preferably 0.8–1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The α-cyanoacrylates of formula (II) wherein $R^3$ is a group having the formula

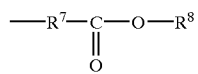

can be prepared according to the procedure described in U.S. Pat. No. 3,995,641 to Kronenthal et al., which is hereby incorporated in its entirety by reference. In the Kronenthal et al. method, such α-cyanoacrylate monomers are prepared by reacting an alkyl ester of an α-cyanoacrylic acid with a cyclic 1,3-diene to form a Diels-Alder adduct which is then subjected to alkaline hydrolysis followed by acidification to form the corresponding α-cyanoacrylic acid adduct. The α-cyanoacrylic acid adduct is preferably esterified by an alkyl bromoacetate to yield the corresponding carbalkoxymethyl α-cyanoacrylate adduct. Alternatively, the α-cyanoacrylic acid adduct may be converted to the α-cyanoacrylyl halide adduct by reaction with thionyl chloride. The α-cyanoacrylyl halide adduct is then reacted with an alkyl hydroxyacetate or a methyl substituted alkyl hydroxyacetate to yield the corresponding carbalkoxymethyl α-cyanoacrylate adduct or carbalkoxy alkyl α-cyanoacrylate adduct, respectively. The cyclic 1,3-diene blocking group is finally removed and the carbalkoxy methyl α-cyanoacrylate adduct or the carbalkoxy alkyl α-cyanoacrylate adduct is converted into the corresponding carbalkoxy alkyl α-cyanoacrylate by heating the adduct in the presence of a slight deficit of maleic anhydride.

Examples of monomers of formula (II) include cyanopentadienoates and α-cyanoacrylates of the formula:

wherein Z is —CH=$CH_2$ and $R^3$ is as defined above. The monomers of formula (III) wherein $R^3$ is an alkyl group of 1–10 carbon atoms, i.e., the 2-cyanopenta-2,4-dienoic acid esters, can be prepared by reacting an appropriate 2-cyanoacetate with acrolein in the presence of a catalyst such as zinc chloride. This method of preparing 2-cyanopenta-2,4-dienoic acid esters is disclosed, for example, in U.S. Pat. No. 3,554,990, which is hereby incorporated in its entirety by reference.

Preferred monomers are alkyl α-cyanoacrylates and more preferably octyl α-cyanoacrylates, especially 2-octyl α-cyanoacrylate. Monomers utilized in the present application should be very pure and contain few impurities (e.g., surgical grade).

The composition nay optionally also include at least one plasticizing agent that imparts flexibility to the polymerized monomer formed on the wound, incision, or abrasion. The plasticizing agent preferably contains little or no moisture and should not significantly affect the polymerization of the monomer.

Examples of suitable plasticizers include acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The composition may also optionally include at least one stabilizing agent that inhibits polymerization. Such stabilizing agents may also include mixtures of anionic stabilizing agents and radical stabilizing agents.

Examples of suitable anionic stabilizing agents include, but are not limited to, sultones (e.g., α-chloro-α-hydroxy-o-toluenesulfonic acid-y-sultone), sulfur dioxide, sulfuric acid, sulfonic acid, lactone, boron trifluoride, organic acids, such as acetic acid or phosphoric acid, alkyl sulfate, alkyl sulfite, 3-sulfolene, alkylsulfone, alkyl sulfoxide, mercaptan, and alkyl sulfide and mixtures thereof. Preferable anionic stabilizing agents are acidic stabilizing agents of organic acids such as acetic acid or phosphoric acid. In embodiments, the amount of sulfur dioxide stabilizer is less than 100 ppm, preferably 5–75 ppm, and more preferably from about 20–50 ppm. The amount of sultone and/or trifluoracetic acid is about 500–3000 ppm.

Examples of suitable radical stabilizing agents include hydroquinone, hydroquinone monomethyl ether, catechol, pyrogallol, benzoquinone, 2-hydroxybenzoquinone, p-methoxy phenol, t-butyl catechol, butylated hydroxy anisole (BHA), butylated hydroxy toluene, and t-butyl hydroquinone. In embodiments, the amount of BHA is about 1,000–5,000 ppm.

Suitable acidic stabilizing agents include those having aqueous $pK_a$ ionization constants ranging from −12 to 7, about −5 to about 7, preferably from about −3.5 to about 6. For example, suitable acidic stabilizing agents include: hydrogen sulfide ($pK_a7.0$), carbonic acid ($pK_a6.4$), triacetylmethane ($pK_a5.9$), acetic acid ($pK_a4.8$), benzoic acid ($pK_a4.2$), 2,4-dinitrophenol ($pK_a4.0$), formic acid ($pK_a3.7$), nitrous acid ($pK_a3.3$), hydrofluoric acid ($pK_a3.2$), chloroacetic acid ($pK_a2.9$), phosphoric acid ($pK_a2.2$), dichloroacetic acid ($pK_a1.3$), trichloroacetic acid ($pK_a0.7$), 2,4,6-trinitrophenol (picric acid) ($pK_a0.3$), trifluoroacetic acid ($pK_a0.2$), sulfuric acid ($pK_a3.0$), sulfurous acid, and mixtures thereof. In embodiments, the amount of trifluoroacetic acid is about 500–1,500 ppm. Combinations of the above stabilizers, such as sulfur dioxide and sulfuric acid, boron trifluoride and sulfuric acid, sulfur dioxide and chloroacetic acid, boron trifluoride and chloroacetic acid, sulfur dioxide and trifluoroacetic acid, and boron trifluoride and triflouroacetic acid can be used.

When adding the acidic stabilizing agents mentioned above to the adhesive composition, the addition of plasticizing agents in amounts ranging from about 0.5 wt. % to about 16 wt. %, preferably from about 3 wt. % to about 9 wt. %, and more preferably from about 5 wt. % to about 7 wt. % provides increased elongation and toughness of the polymerized monomer over polymerized monomers not having plasticizing agents and acidic stabilizing agents.

The concentration of the acidic stabilizing agents utilized may vary depending on the strength of the acid. For example, when using acetic acid, a concentration of 80–200 ppm (wt/wt), preferably 90–180 ppm (wt/wt), and more preferably 100–150 ppm (wt/wt) may be utilized. When using a stronger acid such as phosphoric acid, a concentration range of 20–80 ppm (wt/wt), preferably, 30–70 ppm (wt/wt) and more preferably 40–60 ppm (wt/wt) may be utilized. In embodiments, the amount of trifluoroacetic acid is about 100 to 3000 ppm, preferably 500–1500 ppm. In other embodiments, the amount of phosphoric acid is about 10–200 ppm, preferably about 50–150 ppm, and more preferably about 75–125 ppm.

In addition to the above materials, or in place thereof, the medicament, applicator tip and/or the adhesive composition can also include various other materials that may or may not act as a polymerization initiator or rate modifier, or such materials may be separately applied. For example, the applicator tip and/or the adhesive composition can include a flavorant, such that it imparts a flavor to the adhesive material when the adhesive material is applied to a surface. Incorporation of a flavorant is particularly preferred, for example, when the cyanoacrylate adhesive material is to be applied to oral surfaces, such as to treat stomatitis or cold sores. Such a flavorant can also, in embodiments, be incorporated with the medicament that is applied prior to the adhesive composition. Alternatively, it can be separately applied before or after the medicament.

When a flavorant is to be included, any of the various available and suitable flavorants can be used. Suitable flavorants can be selected, for example, from among fruit oil, vegetable oil, esters, heterocyclic compounds, fruit extract and vegetable extract. In particular, the flavoring additive may be selected from among any of the various known flavoring additives, including, but not limited to, 5-fold orange oil (Florida Chemical Co.), anethole (Aldrich), banana distillate (Florida Chemical Co.), benzaldehyde (Aldrich), clove oil (Humco), cold pressed valencia orange oil (Florida Chemical Co.), cold pressed grapefruit oil (Florida Chemical Co.), cold pressed lemon oil (Florida Chemical Co.), cold pressed lime oil (Florida Chemical Co.), cucumber distillate (Florida Chemical Co.), honey distillate (Florida Chemical Co.), menthol (Aldrich), alkyl salicylates such as methyl salicylate (Lorann Oils or Aldrich), monosodium glutamate, spearmint, wintergreen, cinnamon, citrus, cherry, apple, peppermint, peppermint oil (Humco), peppermint spirit, vanillin (Aldrich), thymol (Aldrich), and ethyl vanillin, mixtures thereof, and the like. The flavorant can also be a sweetener, such as a suitable sugar or sugar substitute. Examples of such sweeteners include, but are not limited to, saccharin, sorbitol, mannitol, aspartame, sucrose, glucose, fructose, and the like. In preferred embodiments, the flavoring additive is a flavoring agent as defined in 21 C.F.R. §172.510, dated Jun. 12, 1989, and §172.515, dated Apr. 1, 1996, the entireties of which are incorporated herein by reference. Flavoring additives are also disclosed in U.S. patent application Ser. No. 09/343, 914, filed Jun. 30, 1999, the entire disclosure of which is incorporated herein by reference.

The flavorant is selected such that it is preferably compatible with the monomer (i.e., does not adversely affect polymerization, bond strength, cure properties, or shelf-life). Preferably, the flavorant is soluble in the monomer composition at room temperature (i.e., 20–25° C.) so that it may be readily solubilized in the monomer composition while the monomer composition is in contact with or passing through the applicator tip. Furthermore, the flavorant is selected such that it is preferably compatible with the applicator tip and any other components that are to be incorporated into or on the applicator tip.

The flavorant is used in an amount to provide the desired flavor level to the final polymerized adhesive. For example, the flavorant can be provided in an amount of, for example, from about 0.001–25.0% by weight of the adhesive composition to be applied. In preferred embodiments, the flavorant is incorporated in an amount of from about 0.2–10.0%, more preferably 0.5–5.0%, of the adhesive composition. Of course, additive amounts outside of these ranges can be readily used depending upon, for example, the desired result to be achieved and the relative flavoring strength of the particular flavorant. The amount of flavorant to be used can be determined by one of ordinary skill in the art based on the present disclosure using known techniques without undue experimentation.

Furthermore, in embodiments, the flavorant can be applied in combination with a delivery substrate to facilitate incorporation of the flavorant into or onto the applicator tip. Where used, suitable delivery substrates include, but are not limited to, waxes, such as carnauba, petroleum and carbowax; gels, such as gelatin, hydroxypropyl methylcellulose, carboxymethylcellulose, and hydroxy-gels; polyethylene glycol; polysorbate; agar; povidone; sodium stearate; starch; powdered sugar; high fructose corn syrup; fructose; glycerin; hydrogenated glucose syrup; sorbitol; mannitol; sucrose; cellulose acetate phthalate; dextrose; polyvinyl alcohol; mixtures thereof; and the like.

Still further, it may be desirable to incorporate a preservative into the flavorant, adhesive composition, or applicator tip in addition to the flavorant, to help preserve and maintain the flavoring effect of the flavorant. The need for such a preservative can depend, for example, upon the concentration and nature of flavorant, or lack thereof. Suitable preservatives generally include the known food preservatives, such as sodium benzoate, salt, citric acid, benzoic acid, sodium nitrite, sodium phosphate, and the like.

Preferably, the flavorant, delivery substrate and/or preservative do not adversely affect the applicator tip, the adhesive composition and/or the medicament. For example, it is preferred that these materials do not adversely affect the aging and/or shelf-life of the materials that the flavorant, delivery substrate and/or preservative are in contact with during storage and/or use.

The compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitrites; carbamates; alcohols; mercaptans; proteins; mixtures of amines, amides, and proteins; active methylene compounds such as cyclic ketones and compounds having a b-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Bisulfites and sulfites useful as the formaldehyde scavenger compound in this invention include alkali metal salts such as lithium, sodium and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like.

Examples of amines useful in this invention include the aliphatic and aromatic amines such as, for example, aniline, benzidine, aminopyrimidine, toluene-diamine, triethylenediamine, diphenylamine, diaminodiphenylamine, hydrazines and hydrazide.

Suitable proteins include collagen, gelatin, casein, soybean protein, vegetable protein, keratin, and glue. The preferred protein for use in this invention is casein.

Suitable amides for use in this invention include urea, cyanamide, acrylamide, benzamide, and acetamide. Urea is a preferred amide.

Suitable alcohols include phenols, 1,4-butanediol, d-sorbitol, and polyvinyl alcohol.

Examples of suitable compounds having a b-dicarbonyl group include malonic acid, acetylacetone, ethylacetone, acetate, malonamide, diethylmalonate or another malonic ester.

Preferred cyclic ketones for use in this invention include cyclohexanone or cyclopentanone.

Examples of suitable heterocyclic compounds for use as the formaldehyde scavenger in this invention are disclosed, for example, in U.S. Pat. No. 4,127,382 (Perry) which is hereby incorporated in its entirety by reference. Such heterocyclic compounds include, for example, benzimidazole, 5-methyl benzimidazole, 2-methylbenzimidazole, indole, pyrrole, 1,2,4-triazole, indoline, benzotriazole, indoline, and the like.

A preferred formaldehyde scavenger for use in this invention is sodium bisulfite.

In practicing the present invention, the formaldehyde concentration reducing agent, e.g., formaldehyde scavenger compound, is added in an effective amount to the cyanoacrylate. The "effective amount" is that amount sufficient to reduce the amount of formaldehyde generated during subsequent in vivo biodegradation of the polymerized cyanoacrylate. This amount will depend on the type of active formaldehyde concentration reducing agent, and can be readily determined without undue experimentation by those skilled in the art.

The formaldehyde concentration reducing agent may be used in this invention in either free form or in microencapsulated form. Other compositions are exemplified by U.S. patent application Ser. No. 08/714,288, incorporated by reference herein in its entirety.

When microencapsulated, the formaldehyde concentration reducing agent is released from the microcapsule continuously over a period of time during the in vivo biodegradation of the cyanoacrylate polymer.

For purposes of this invention, the microencapsulated form of the formaldehyde concentration reducing agent is preferred because this embodiment prevents or substantially reduces polymerization of the cyanoacrylate monomer by the formaldehyde concentration reducing agent, which increases shelf-life and facilitates handling of the monomer composition during use.

Microencapsulation of the formaldehyde scavenger can be achieved by many known microencapsulation techniques. For example, microencapsulation can be carried out by dissolving a coating polymer in a volatile solvent, e.g., methylene chloride, to a polymer concentration of about 6% by weight; adding a formaldehyde scavenger compound in particulate form to the coating polymer/solvent solution under agitation to yield a scavenger concentration of 18% by weight; slowly adding a surfactant-containing mineral oil solution to the polymer solution under rapid agitation; allowing the volatile solvent to evaporate under agitation; removing the agitator; separating the solids from the mineral oil; and washing and drying the microparticles. The size of the microparticles will range from about 0.001 to about 1000 microns.

The coating polymer for microencapsulating the formaldehyde concentration reducing agent should be polymers which undergo in vivo bioerosion, preferably at rates similar to or greater than the cyanoacrylate polymer formed by the monomer, and should have low inherent moisture content. Such bioerosion can occur as a result of the physical or chemical breakdown of the encapsulating material, for example, by the encapsulating material passing from solid to solute in the presence of body fluids, or by biodegradation of the encapsulating material by agents present in the body.

Examples of coating materials which can be used to microencapsulate the formaldehyde concentration reducing agent include polyesters, such as polyglycolic acid, polylactic acid, poly-1,4-dioxa-2-one, polyoxaltes, polycarbonates, copolymers of polyglycolic acid and polylactic acid, polycaprolactone, poly-b-hydroxybutyrate, copolymers of epsilon-caprolactone and delta-valerolactone, copolymers of epsilon-caprolactone and DL-dilactide, and polyester hydrogels; polyvinylpyrrolidone; polyamides; gelatin; albumin; proteins; collagen; poly(orthoesters); poly(anhydrides); poly(alkyl-2-cyanoacrylates); poly(dihydropyrans); poly(acetals); poly(phosphazenes); poly(urethanes); poly(dioxinones); cellulose; and starches.

Examples of surfactants which can be added to the mineral oil include those commercially available under the designations Triton X-100™ (octoxynol from Rohm and Haas), Tween 20™ (polysorbate 20 from ICI Americas), and Tween 80™ (polysorbate 80 from ICI Americas).

The composition may also optionally include at least one thickening agent.

Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate).

To improve the cohesive strength of adhesives formed from the compositions of this invention, difuictional monomeric cross-linking agents may be added to the monomer compositions of this invention. Such crosslinking agents are known. U.S. Pat. No. 3,940,362 to Overhults, which is hereby incorporated in its entirety by reference, discloses such cross-linking agents. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). A catalytic amount of an amine activated free radical initiator or rate modifier may be added to initiate polymerization or to modify the rate of polymerization of the cyanoacrylate monomer/crosslinking agent blend.

The compositions of this invention may further contain fibrous reinforcement and colorants, i.e., dyes and pigments. Examples of suitable fibrous reinforcement include PGA microfibrils, collagen microfibrils, cellulosic microfibrils, and olefinic microfibrils. Examples of suitable colorants include 1-hydroxy-4-[4-methylphenyl-amino]-9,10 anthracenedione (D+C violet No. 2); disodium salt of 6-hydroxy-5-[(4-sulfophenyl)axo]-2-naphthalene-sulfonic acid (FD+C Yellow No. 6); 9-(o-carboxyphenOyl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato (2-)] copper.

Other compositions that are contemplated by the present invention are exemplified by U.S. Pat. Nos. 5,624,669; 5,582,834; 5,575,997; 5,514,371; 5,514,372; and 5,259,835; the disclosures of all of which are hereby incorporated in their entirety by reference.

EXAMPLE

A sample of 120 microliters of 1000 ppm BAC solution in methanol was tested for its initiation property with 2-octyl cyanoacrylate in accordance with the method described above. The following polymerization times were obtained:

| Sample Number | Set Time (seconds) |
| --- | --- |
| 1 | 109 |
| 2 | 106 |
| 3 | 111 |
| 4 | 121 |
| 5 | 102 |
| 6 | 101 |
| 7 | 109 |
| 8 | 57 |
| 9 | 126 |

While the invention has been described with reference to preferred embodiments, the invention is not limited to the specific examples given, and other embodiments and modifications can be made by those skilled in the art without departing from the spirit and scope of the invention.

What is claimed is:

1. A method of delivering a medicament to a patient, comprising:
   applying a pharmaceutically effective amount of a medicament to a tissue of said patient, and
   applying a polymerizable monomer composition onto the medicament,
   wherein the medicament is a polymerization initiator or polymerization rate accelerator and causes polymerization of the monomer composition to form a polymeric adhesive covering on said tissue,
   wherein the medicament is selected from the group consisting of antibiotics, antimicrobials, antiseptics, bacteriocins, bacteriostats, disinfectants, steroids, anti-fimgal agents, anti-inflammatory agents, antibacterial agents, antiviral agents, antitumor agents, growth promoters, and mixtures thereof and
   wherein the polymerizable monomer is a 1,1-disubstituted ethylene monomer.

2. The method of claim 1, wherein the medicament is crystal violet.

3. The method of claim 1, wherein the medicament is selected from the group consisting of quaternary ammonium halides, chlorhexidine sulfate, gentamicin sulfate, hydrogen peroxide, neomycin sulfate, quinolone thioureas, salts of silver, copper compounds, sodium hypochlorite, antioxidants, salts of sulfadiazine, and mixtures thereof.

4. The method of claim 1, wherein the medicament is selected from the group consisting of quaternary ammonium halides, salts of sulfadiazine, and salts or complexes of silver or zinc or copper.

5. The method of claim 4, wherein the medicament is a quaternary ammonium halide selected from the group consisting of alkylbenzyldimethylammonium chloride with an alkyl containing 6–18 carbon atoms, its pure components, or mixtures thereof; and benzethonium chloride.

6. The method of claim 4, wherein the medicament is a salt of sulfadiazine selected from the group consisting of a silver salt, a sodium salt, and a zinc salt.

7. The method of claim 4, wherein the medicament is a zinc compound selected from the group consisting of zinc salts of cyanoacrylic acid, zinc salts of cyanoacetic acid, zinc salts of dicyanoglutaric acid, zinc salts of rosin, zinc oxide, zinc salts of polycyanoacrylic acid, zinc salts of polyacrylic acid, zinc bacitracin, zinc salicylate, zinc stearate, zinc citrate, zinc lactate, and mixtures thereof.

8. The method of claim 1, wherein the medicament has a local pharmaceutical effect on the tissue to which it is applied.

9. The method of claim 1, wherein the medicament has a systemic pharmaceutical effect on said patient.

10. The method of claim 9, wherein the medicament is an anion, participates in radical generation, is an ion pair, or is a radical.

11. The method of claim 1, wherein the polymerizable monomer is an α-cyanoacrylate.

12. The method of claim 11, wherein the α-cyanoacrylate is selected from the group consisting of ethyl, butyl and octyl α-cyanoacrylate.

13. The method of claim 11, wherein the medicament is applied by spraying, brushing, swabbing, dripping, wiping, or dusting.

14. The method of claim 1, wherein the polymerizable monomer composition is applied by spraying, brushing, swabbing, or dripping.

15. The method of claim 1, further comprising applying a flavorant to said tissue.

16. The method of claim 15, wherein said tissue is oral tissue or a lip.

17. The method of claim 16, wherein said flavorant is combined with said medicament.

18. The method of claim 16, wherein said flavorant is applied in a separate step.

19. The method of claim 16, wherein said flavorant is applied as a component of said monomer composition.

20. The method of claim 15, wherein the flavorant is selected from the group consisting of 5-fold orange oil, anethole, banana distillate, benzaldehyde, clove oil, cold pressed valencia orange oil, cold pressed grapefruit oil, cold pressed lemon oil, cold pressed lime oil, cucumber distillate, honey distillate, menthol, alkyl salicylates, monosodium glutamate, spearmint, wintergreen, cinnamon, citrus, cherry, apple, peppermint, peppermint oil, peppermint spirit, vanillin, thymol, and ethyl vanillin.

21. The method of claim 1, wherein the method is used to close or seal a wound.

22. The method of claim 21, wherein the wound is an internal wound.

23. The method of claim 21, wherein the wound is a superficial wound.

24. The method of claim 21, further comprising suturing or stapling said wound before or after applying said medicament.

25. The method of claim 1, wherein the method is used to treat tissues affected by at least one member selected from the group consisting of minor cuts, scrapes, irritations, compromised skin, abrasions, lacerations, burns, sores, chaffed skin, stomatitis, and surgical wounds.

26. The method of claim 1, wherein the method is used to dress burns.

27. The method of claim 1, wherein the method is used to treat stomatitis.

28. The method of claim 1, wherein the tissue comprises blood vessels.

29. The method of claim 1, wherein the tissue comprises a cold sore.

30. The method of claim 1, wherein the patient is an animal.

31. The method of claim 1, wherein the polymerization is complete in less than 300 seconds at a temperature of 21–25° C.

32. A kit for delivering a medicament to a patient, comprising a package containing:

a first container that contains a polymerizable monomer composition, and a second container that contains a medicament, wherein said medicament is a polymerization initiator or polymerization rate accelerator and causes polymerization of the monomer composition to form a polymeric adhesive, and wherein the polymerizable monomer is a 1,1-disubstituted ethylene monomer.

33. The kit of claim 31, wherein the medicament is present in a pharmaceutically effective amount for topical application on tissue.

34. The kit of claim 31, wherein the superficial tissue is skin.

35. The kit of claim 31, wherein the second container further contains a material selected from the group consisting of antibiotics, antimicrobials, antiseptics, bacteriocins, bacteriostats, disinfectants, and mixtures thereof.

36. The kit of claim 32, wherein the polymerizable monomer is an α-cyanoacrylate.

37. The kit of claim 36, wherein the α-cyanoacrylate is selected from the group consisting of ethyl, butyl and octyl α-cyanoacrylate.

38. The kit of claim 36, wherein the medicament is crystal violet.

39. The kit of claim 36, wherein the medicament is selected from the group consisting of quaternary ammonium halides, salts of sulfadiazine, and salts or complexes of silver or zinc or copper.

40. The kit of claim 39, wherein the medicament is a quaternary ammonium halide selected from the group consisting of alkylbenzyldimethylammonium chloride with an alkyl containing 6–18 carbon atoms, its pure components, or mixtures thereof; and benzethonium chloride.

41. The kit of claim 39, wherein the medicament is a salt of sulfadiazine selected from the group consisting of a silver salt, a sodium salt, and a zinc salt.

42. The kit of claim 39, wherein the medicament is a zinc compound selected from the group consisting of zinc salts of cyanoacrylic acid, zinc salts of cyanoacetic acid, zinc salts of dicyanoglutaric acid, zinc salts of rosin, zinc oxide, zinc salts of polycyanoacrylic acid, zinc salts of polyacrylic acid, zinc bacitracin, zinc salicylate, zinc stearate, zinc citrate, zinc lactate, and mixtures thereof.

43. The kit of claim 36, wherein the kit is sterilized.

44. The kit of claim 32, further containing a third container that contains a flavorant.

45. The kit of claim 32, wherein at least one of said first container and said second container also contains a flavorant.

46. The kit of claim 32, wherein the patient is an animal.

47. The kit of claim 32, wherein the polymerizable monomer polymerizes in less than 300 seconds at a temperature of 21–25° C. when contacted with said medicament.

* * * * *